United States Patent
Suaning et al.

(10) Patent No.: US 9,205,272 B2
(45) Date of Patent: Dec. 8, 2015

(54) METHOD OF POWER AND DATA TRANSFER IN IMPLANTABLE ELECTRONIC DEVICES

(75) Inventors: Gregg Jorgen Suaning, New South Wales (AU); Phil Byrnes-Preston, New South Wales (AU); Torsten Lehmann, New South Wales (AU)

(73) Assignee: NewSouth Innovations Pty Limited (AU)

( * ) Notice: Subject to any disclaimer, the term of this patent is extended or adjusted under 35 U.S.C. 154(b) by 394 days.

(21) Appl. No.: 13/501,714

(22) PCT Filed: Oct. 12, 2010

(86) PCT No.: PCT/AU2010/001341
§ 371 (c)(1), (2), (4) Date: Aug. 30, 2012

(87) PCT Pub. No.: WO2011/044616
PCT Pub. Date: Apr. 21, 2011

(65) Prior Publication Data
US 2012/0316620 A1    Dec. 13, 2012

(30) Foreign Application Priority Data
Oct. 12, 2009  (AU) ............................... 2009904958

(51) Int. Cl.
| | |
|---|---|
| *A61N 1/00* | (2006.01) |
| *A61N 1/378* | (2006.01) |
| *A61N 1/372* | (2006.01) |
| *A61N 1/08* | (2006.01) |
| *A61N 1/05* | (2006.01) |
| *A61N 1/37* | (2006.01) |

(52) U.S. Cl.
CPC ................ *A61N 1/3787* (2013.01); *A61N 1/08* (2013.01); *A61N 1/37211* (2013.01); *A61N 1/0541* (2013.01); *A61N 1/3718* (2013.01); *A61N 1/37258* (2013.01)

(58) Field of Classification Search
CPC ................... A61N 1/378–1/3787; A61N 1/08; A61N 1/372–1/37288
USPC ....................................................... 607/1–76
See application file for complete search history.

(56) References Cited

U.S. PATENT DOCUMENTS

| | | | | |
|---|---|---|---|---|
| 4,363,324 A | * | 12/1982 | Kusserow | ........................ 607/64 |
| 4,592,359 A | * | 6/1986 | Galbraith | ......................... 607/57 |
| 6,275,735 B1 | * | 8/2001 | Jarding et al. | ................... 607/53 |
| 7,260,436 B2 | | 8/2007 | Kilgore et al. | |
| 2004/0015211 A1 | | 1/2004 | Nurmikko et al. | |
| 2004/0059396 A1 | | 3/2004 | Reinke et al. | |

(Continued)

OTHER PUBLICATIONS

International Search Report and Written Opinion issued in application No. PCT/AU2010/001341 on Dec. 1, 2010.

*Primary Examiner* — Scott Getzow
(74) *Attorney, Agent, or Firm* — Knobbe Martens Olson & Bear LLP

(57) ABSTRACT

A system for transferring data and power between electronic devices implanted in a patient is described. The system comprises a first unit and a second unit that in use are both implanted in the patient and a cable connecting the first unit and the second unit. The first unit comprises a current supply unit that supplies a selected current output to the second unit via the cable and a processor configured to anticipate an action to be performed by the second unit and to select the current output dependent on the anticipated action.

23 Claims, 2 Drawing Sheets

(56) References Cited

U.S. PATENT DOCUMENTS

| | | |
|---|---|---|
| 2004/0193222 A1 | 9/2004 | Sullivan |
| 2007/0156204 A1* | 7/2007 | Denker et al. ............... 607/61 |
| 2009/0048524 A1 | 2/2009 | Wildau et al. |
| 2009/0177252 A1* | 7/2009 | Craig ............................ 607/62 |
| 2009/0182388 A1 | 7/2009 | Von Arx et al. |

* cited by examiner

METHOD OF POWER AND DATA TRANSFER IN IMPLANTABLE ELECTRONIC DEVICES

FIELD OF THE INVENTION

The invention relates to methods of power and data transfer between electronic devices that are implanted in a patient.

BACKGROUND OF THE INVENTION

Medical implants for uses such as therapeutic electrical neurostimulation must be capable of functioning in a safe, non-injurious fashion for the duration of their operation. Common modes of device failure include the breach of insulation between a device and the patient's tissue. Insulation failures may lead to the patient becoming exposed to unregulated voltage supplies capable of doing harm. Corrosion of components of the device may ultimately lead to device failure.

There is in general a need for devices to be compact if they are to be implanted in a patient's body.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

It is an object of the present invention to substantially overcome, or at least ameliorate, one or more disadvantages of existing arrangements. Aspects of the invention assist to reduce or eliminate the severity of the effects of failure modes of implanted electronic devices.

According to a first aspect of the invention there is provided a system for transferring data and power between electronic devices implanted in a patient, the system comprising: a first unit and a second unit that in use are both implanted in the patient; and a cable connecting the first unit and the second unit, wherein the first unit comprises: a current supply unit that supplies a selected current output to the second unit via the cable; and a processor configured to anticipate an action to be performed by the second unit and to select the current output dependent on the anticipated action.

The processor may select the current output from the group consisting of: a quiescent current output that has a magnitude sufficient to power the second unit in a quiescent state; and a stimulation current output that has a magnitude matched to an expected power requirement for the second unit to perform the anticipated action.

The second unit may comprise a rectifier to rectify the current output received via the cable to power the second unit.

The current output may be a square current waveform having intermittent transitions of polarity and the processor changes the polarity while the loading of the current supply unit is below a minimum threshold.

The second unit may consist of a housing and a single integrated circuit without additional discrete components that affect the size of the second unit.

The system may comprise one or more electrodes operable to apply stimulus signals to biological tissue of the patient, the second unit comprising a stimulus controller to control operation of the one or more electrodes.

The stimulus controller may control the one or more electrodes dependent on control information received from the first unit via the cable.

The stimulus controller may comprise means for current limitation such that a current to the one or more electrodes is negligible unless the received control information specifies stimulation by the one or more electrodes. The means for current limitation may comprise a push-pull circuit.

The cable in one arrangement comprises two wires and the first unit may comprise a voltage measuring unit that measures a voltage across the wires.

The processor may compare the measured voltage across the wires to an anticipated voltage associated with the anticipated action of the second unit, and may take remedial action if the measured voltage differs from the anticipated voltage, the remedial action including at least one of: reducing the output current of the current supply unit; stopping the output current of the current supply unit; and limiting the voltage across the wires.

The system may comprise a current measuring unit that monitors a current in at least one electrode after stimulation of the at least one electrode has ended, wherein the second unit alerts the first unit to a fault condition if the monitored current exceeds a threshold.

The system may comprise means for reducing a charge imbalance between the first unit and the second unit including for example at least one capacitor connected in series between the current supply unit and the cable.

The current output supplied by the first unit to the second unit may be intermittently reversed in polarity and the system may act to equalise an accumulated time spent at each polarity.

The cable may comprise two wires joining the first unit and the second unit, wherein in use the current supply unit supplies each wire with a current equal in magnitude and opposite in polarity to the current carried by the other wire.

The first unit may comprise switching means to reverse the polarity of the current carried by the wires, the switching means acting to reverse the polarity of the wires substantially simultaneously.

The processor may select the magnitude of the current supplied to the two wires dependent on an anticipated power requirement of the second unit.

Data may be encoded in the quiescent current output supplied to the second unit.

According to another aspect of the invention there is provided a system for transferring data and power between electronic devices implanted in a patient, the system comprising: a first unit and a second unit that in use are both implanted in the patient; and a cable connecting the first unit and the second unit, wherein the first unit comprises: a current supply unit that supplies a selected current output to provide data and power to the second unit via the cable; and a processor configured to intermittently reverse a polarity of the supplied current, wherein the processor reverses the polarity while a loading of the current supply unit is at or near a minimum.

According to a further aspect there is provided a method for transferring data and power via a cable comprising two wires between a first unit and a second unit implanted in a patient, the method comprising: anticipating an action to be taken by the second unit; and selecting a current output to be output by the first unit via the cable, wherein the selection is dependent on an expected power requirement of the second unit for the anticipated action.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

Embodiments of the present invention are described below with reference to the drawings, in which.

DETAILED DESCRIPTION OF THE EMBODIMENTS

Figure 1:
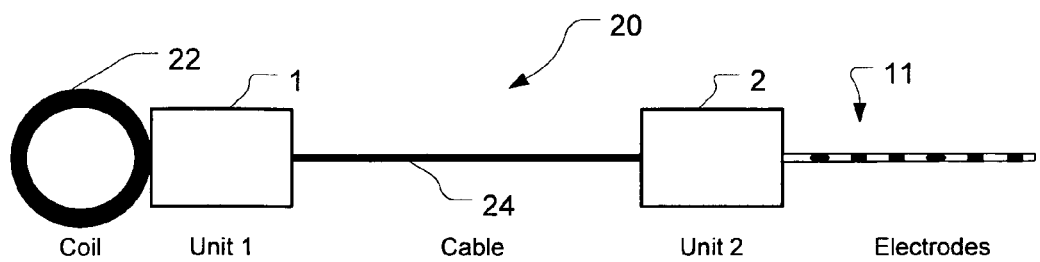
FIG. 1 is a schematic diagram of a medical implant system including a first unit connected to a second unit by a cable.

FIG. 1 shows an illustrative example of a medical implant system 20 for the purpose of electrical stimulation of neural tissue. In this illustrative example, the coil 22 is inductively coupled to an external transmitting coil and associated circuitry (not shown) outside the body for purposes of passing data from or to the outside the body to control the implant function. The coil 22 is coupled to implanted Unit 1. For example the output of the coil 22 may be communicated to Unit 1 by means of a transformer (not shown). Rectification of the data signal received by Unit 1 is a common method of powering such a medical implant. Unit 1 receives the data, rectifies the power and stores it, for example in a capacitor, to provide a relatively stable, but otherwise unregulated DC voltage supply $V_{STIM}$. Division and/or regulation of $V_{STIM}$ may provide a stable DC voltage supply that, for example, may be used to power digital circuitry within Unit 1. This regulated supply is denoted $V_{LOGIC}$. Both $V_{STIM}$ and $V_{LOGIC}$ are relative to a 0 V reference.

In this example, data and power are communicated between Unit 1 and Unit 2 via a two wire cable 24.

Figure 2:
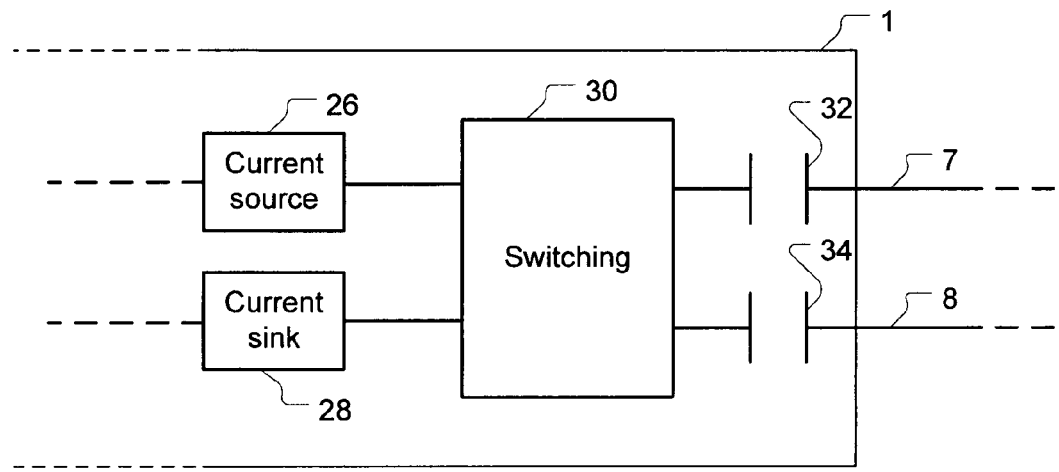
FIG. 2 is a functional block diagram of a portion of the first unit in the system of FIG. 1.

An example of one suitable arrangement is illustrated in schematic form in FIG. 2, which shows a detail of Unit 1. The cable 24 has two wires 7, 8 which each carry a constant current of opposite polarity to the current carried by the other wire. Current source 26 and current sink 28 drive the currents carried by wires 7, 8. A switching circuit 30 determines which of the wires is, connected to the current source and the current sink. The switching circuit thus enables the polarity of the currents to be changed.

A capacitor 32 is provided in series with wire 7 and a capacitor 34 is provided in series with wire 8. As discussed in more detail below, the series capacitors 32, 34 serve to reduce any charge imbalance between Unit 1 and Unit 2 and also to dereference electrical signals passed along the wires 7, 8.

In other arrangements an additional line or lines may also pass data signals between Unit 1 and Unit 2 via the Cable 24.

Figure 4:
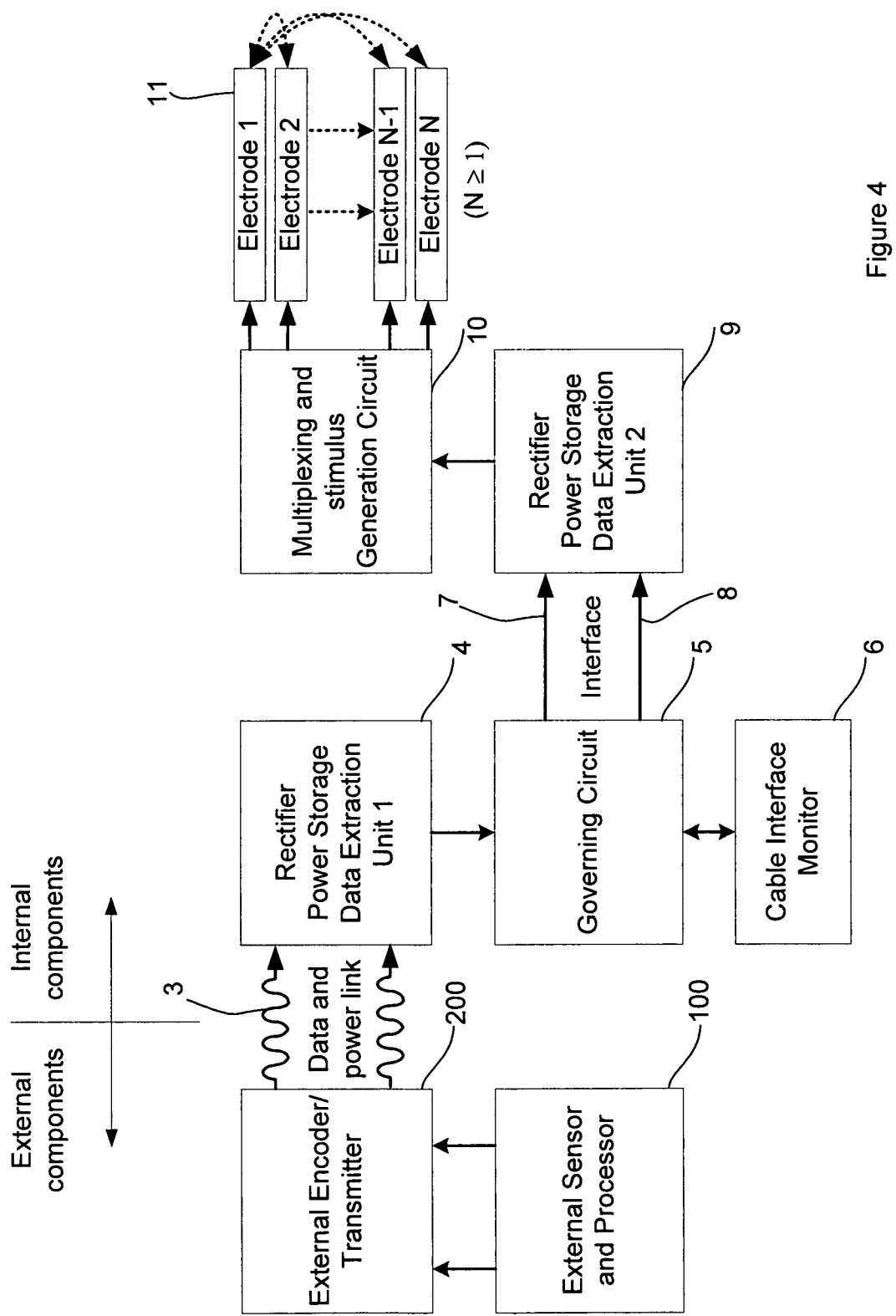
FIG. 4 is a functional block diagram of the medical implant system together with external components.

FIG. 4 shows a functional block diagram of the system 20. Unit 1 includes functional modules 4, 5 and 6. External components 100 and 200 communicate data and power to Unit 1, as described in more detail below with reference to a cochlear implant system. Module 4 serves to rectify the incoming signal and to store power for the operation of the implanted system. Module 4 also extracts data encoded in the incoming signal, and may also encode data to be conveyed to the external components. A governing circuit 5 generates the signal applied to wires 7 and 8. The current source 26, current sink 28, switching circuit 30 and capacitors 32, 34 may form part of the governing circuit 5.

A cable interface monitor 6 monitors parameters of the signals carried by the wires 7, 8. The monitor includes a voltage measurement monitoring the voltage across the wires.

Electronics within Unit 2 create one or more signals that are connected to one or more electrodes 11. The form of these signals may take the form of constant current, charge-balanced, biphasic waveforms for the purpose of physiological excitation of neural tissue. These signals are referred to as electrical stimuli in their plural form, electrical stimulus in their singular form. The general form (either single or plural electrical stimuli) is called electrical stimulation.

As illustrated in FIG. 4, the electronics within Unit 2 include functional modules 9 and 10. Module 9 extracts data from the incoming signal and rectifies the signal to power operation of Unit 2 and the associated electrodes 11. Functional module 10 controls the operation of the electrodes 11 and provides the electric charge required for the electrodes to stimulate the patient's adjacent tissue. The dashed arrows in FIG. 4 indicate current flowing through the patient's tissue.

An example of a method for multiplexing a plurality of electrodes such as electrodes 11 is described in U.S. patent application Ser. Nos. 12/275,094 and 11/112,571 "Electrode multiplexing method for retinal prosthesis", the earlier of which was filed on 25 Apr. 2005 in the name of Suaning et al and published as US2006/0241753. The contents of these applications are incorporated by reference herein.

In one failure mode scenario, the insulation on the Cable 24 is damaged, and one or more of the signals inside the Cable become exposed to biological fluid or tissue. Upon delivery of electrical stimulation to the electrodes 11, a circuit may be formed via the biological fluid or tissue to the exposed wires in the Cable. In this failure mode, significant, largely unregulated current may flow through the patient's tissue, potentially causing severe pain, spasm, tissue damage, or other adverse effects. This failure mode may manifest itself by way of a single fault, that is, damage to the insulation on the Cable.

Corrosion may result from insulation failure that exposes an interconnecting joint, such as where the Cable leaves or enters Unit 1 or Unit 2, to an electrolyte. DC current, passed through the joint during operation of the implant can induce galvanic corrosion. Moreover, the accumulation of charge on metals exposed to biological tissue is known to have adverse effects on the tissue. Passage of alternating current (AC) is a known method of addressing this issue as no net DC and therefore no accumulation of charge occurs in this instance.

The reduction of size of either Unit 1 or Unit 2, but in particular Unit 2, is often desirable in order to establish a stable, minimally-invasive device at the targeted implantation site. In the ideal case, Unit 2 may only consist of an integrated electronic circuit and its protective housing. Additional components such as discrete capacitors or an isolation transformer may be too large to be practical. The absence of these relatively large, discrete capacitors limits the ability of Unit 2 to receive AC from Unit 1 via the Cable 24 and condition the AC such that it can be used to power Unit 2 with a stable, relatively ripple-free DC voltage supply as is required for stable operation.

The system and method described herein enables power and data to be passed between Unit 1 and Unit 2 by way of the Cable while reducing or eliminating the risks associated with the common failure modes described above. The described system shows two units. It will be appreciated that the methods described also have application to systems having more than two implanted units. For example, one or more master units may drive a plurality of slave units.

The following paragraphs describe various attributes of the system 20.

Attribute 1:

The method includes anticipation of the operation of Unit 2 within Unit 1. As the controlling data for Unit 2 passes through Unit 1 on its way to Unit 2, all behaviour of Unit 2 is known at Unit 1. By anticipating the behaviour of Unit 2, Unit 1 can limit the electrical power delivered to Unit 2 such that only the required magnitude to provide (e.g.) quiescent power and stimulus delivery is delivered to Unit 2. In this way, should a fault occur, the effect will be substantially reduced relative to one in which an unregulated supply of current is accessible.

In one arrangement a look-up table may be provided that stores data indicating what current Unit 2 requires for a specified task, for example supplying electrical charge to specified electrodes 11. A governing circuit or processor in Unit 1 may retrieve the current values appropriate to an anticipated task and set the current supplied to wires 7 and 8 to match the retrieved current values.

Attribute 2:

Typically, AC is delivered in a sinusoidal waveform then rectified and regulated in order to resolve a DC voltage supply. This process typically requires diodes to rectify the signal, and relatively large capacitors to smooth the transitions. The existence of discrete components such as capacitors is undesirable in Unit 2 owing to size constraints. To address this issue for system 20, a square current waveform is sent from Unit 1 to Unit 2. Rectification of the waveform takes place by an appropriate rectification method (e.g. a FET switch bridge, or rectifying diodes).

Attribute 3:

In rectifying the signal, the transition of polarity on the square current waveform described in Attribute 2 is the principal source of so-called 'ripple' on an otherwise stable supply. To address this issue in system 20, polarity changes only when the loading of the circuit is at or near a minimum (for example between stimulation events or between stimulation phases). In this way, the storage capacitors within Unit 2 can be small in capacitance, and therefore incorporated within the silicon chip that ideally contains the circuitry of Unit 2 in its entirety. The alternative is a large, discrete capacitor (in both size and capacitance) that would be capable of sustaining the drawn current from the supply during polarity transition at times of high power requirements.

Figure 3:
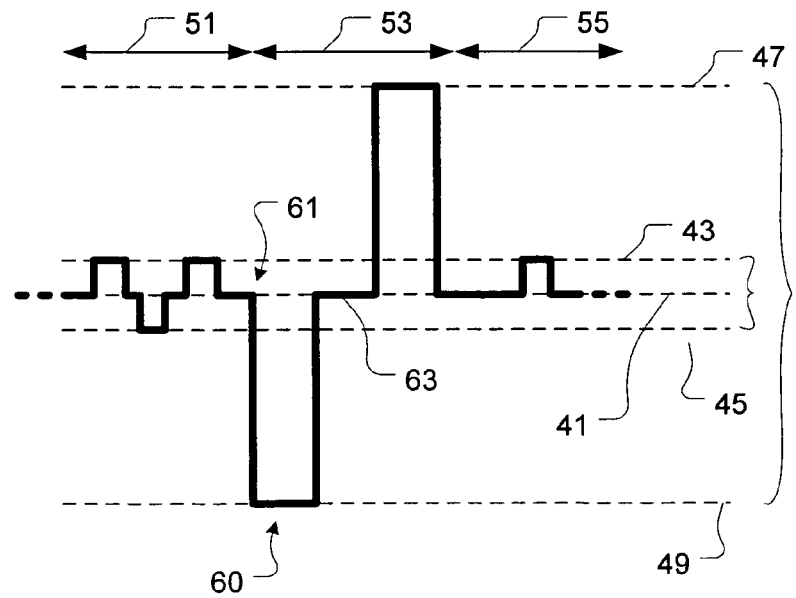
FIG. 3 is a schematic example of a current signal sent form the first unit to the second unit.

FIG. 3 is an illustrative example of a current signal 60 carried on cable 24 between Unit 1 and Unit 2. FIG. 3 plots current magnitude against time. The base level is indicated by line 41. In this example, the current magnitude is selected from two levels. A quiescent magnitude, indicated by lines 43 and 45, is appropriate when Unit 2 is not delivering electrical stimulation. When a stimulation event is anticipated, Unit 1 supplies a larger current magnitude, for example that indicated by lines 47 and 49.

Transitions of polarity, for example the transition 61, occur when the circuit loading is at or near a minimum.

The illustrated waveform 60 includes a first quiescent period 51, a stimulation period 53 and a further quiescent period 55. Data may be transmitted from Unit 1 to Unit 2 during the quiescent periods 51, 55 by encoding the data as a series of pulses. The encoding may be performed to balance out pulses of opposite polarity. This assists in avoiding charge imbalances developing between unit 1 and unit 2. The data signal in periods 51 and 55 of FIG. 3 is merely illustrative and is not intended to demonstrate any particular coding scheme.

In the example, the stimulation output during period 53 includes a first pulse of magnitude 49 and a second pulse of equal and opposite magnitude 47, separated by inter-stimulus gap 63 in which the current is at base level 41. The length of the first and second pulses is preferably the same, to avoid charge imbalances. The example shows a single stimulation magnitude 47, 49. Further stimulation magnitudes may be defined and the governing circuit or processor of Unit 1 may select from a set of different current magnitudes to match the output power of Unit 1 to the anticipated requirements of Unit 2 for different tasks.

In some embodiments, a data signal is superimposed on the stimulation output, providing for communication from Unit 1 to Unit 2. As is typical in communication system design, the data signal is selected to have a magnitude that provides a sufficient expected signal to noise ratio to be detected after transmission. The data signal may also be encoded using a dc-neutral or substantially dc-neutral coding scheme, for example Manchester coding or bipolar coding, to avoid charge imbalance. Another encoding method may be used, particularly if there is sufficient leakage current to maintain any dc bias of the data signal down.

Attribute 4:

With the objective being to minimise or eliminate the flow of current through biological tissue in any fault condition within the implant, a so-called 'push-pull' circuit is used in Unit 2 when delivering current to the electrodes 11. In this way, even if an extraneous path to circuit ground is accessible (e.g. by way of insulation failure), the current that can flow into tissue can be no more than would have otherwise flowed through the tissue had there been no fault. With the exception of a change in the path of the flow of current, adverse effects associated with this fault mode are reduced or eliminated.

Attribute 5:

Monitoring of the voltage across the cable 24 (e.g. across wires 7 and 8) connecting Unit 1 to Unit 2 provides diagnostic data that can aid in the detection of faults. In Attribute 1, the behaviour of Unit 2 is anticipated in Unit 1 by way of monitoring of the data stream containing controlling data for unit 2. The voltage across the Cable connecting Unit 1 to Unit 2 can be further estimated under fault-free conditions. Detection of deviation from these fault-free conditions can be observed by monitoring this voltage and comparing it against the anticipated voltage. Remedial action may be taken, for example by reducing or stopping the flow of current, or by limiting the voltage on the supply line between Unit 1 and Unit 2 in the event that a fault is detected.

Furthermore, a reverse-telemetry circuit can further alert the user or clinician of the nature of the fault mode. In one illustrative example of the benefits of Attribute 5, a short circuit across two electrodes will increase the loading of the circuit, and therefore alter the anticipated voltage across the Cable connecting Unit 1 and Unit 2.

Measuring the voltage across the cable 24 provides a means for unit 1 to detect information coming from unit 2. Within unit 2 the loading of the circuit may be varied to cause changes in the voltage detected in unit 1.

Attribute 6:

A potential fault mode includes breach of insulation of one of the wires within the Cable. To detect this fault mode, a detector such as a high-impedance operational amplifier is connected in parallel to one or more (e.g. all) electrode(s) 11 during the post-stimulus shortening period. Towards the end of this period, after the potentials on all electrodes have reached equilibrium, no current should be flowing from the electrodes to the shortening potential. If the detector measures any extraneous current, a fault is indicated and this may be conveyed to unit 1 so that remedial action may be taken. For example the circuit loading may be increased. This will trigger the voltage monitoring described in attribute 5 and thus instigate remedial action.

In another illustrative example, the existence of a fault condition could be assessed by passing current directly into a monitoring electrode with no return path configured and assessing whether any steady state currents, indicative of a fault-related leakage path existed. If a steady state current is detected, unit 1 may be alerted to the fault to enable remedial action such as stopping current flow.

Attribute 7:

Further to Attribute 2, provision of current between Unit 1 and Unit 2 via the series decoupling capacitors 32, 34 creates a situation such that charge imbalance between units manifests itself in a rapid change in the voltage across the current source 26 or sink 28 that is out of balance with the other. This will cause the current source or sink to enter into voltage compliance and thus effect charge balance.

Operation of Implanted System

Incoming RF data and power, for example in the form of sinusoidal voltage waveforms, are detected and rectified respectively within Unit 1. The processed waveforms provide Unit 1 with a description of the stimuli to be delivered, and energy through which to operate.

In typical operation of the implant 20 as a whole, at least one electrode delivers electrical stimulus. The incoming RF data stream contains all of the attributes describing the electrical stimulus or stimuli to be delivered and so contains sufficient information for unit 1 to determine the current requirements of Unit 2. If an alternative source is not present the RF stream may be rectified and stored as a DC voltage in a capacitor. This voltage may be further regulated to provide a stable, fixed supply voltage for subsequent use by both Unit 1 and Unit 2. Electronics within Unit 1 query the data contained within the RF stream and determine the current that will be required by Unit 2 in the delivery of the next event of electrical stimulation. In the period of time between electrical stimulation events, the power requirements of Unit 2 are at or close to the quiescent levels of the Unit 2 electronics. As a result, the effect of switching the polarity of the power to Unit 2 during this time has substantially reduced ripple effects on a rectified energy supply coming from Unit 1. As such, the capacitance necessary to smooth these ripple effects is substantially reduced, and it becomes possible to implement the functions of unit 2 on an integrated circuit or 'chip'.

By cycling the polarity of the power coming from Unit 1, instructions to dictate Unit 2 behaviour can be resolved. For example, pulses sent to unit 2 during the quiescent periods 51, 53 in FIG. 3 may encode controlling data for unit 2.

Rectification of the power signal can be used to power Unit 2. Immediately prior to, or coincident to the onset of electrical stimulation, the power being supplied by Unit 1 to Unit 2 is increased in order to supply sufficient power to drive the stimulus or stimuli being delivered. Unit 1 will maintain a balance in net charge by reversing the polarity of the power signal at various times such as during the inter-stimulus gap 63 illustrated in FIG. 3. In an alternative arrangement the current to unit 2 remains constant throughout the time between quiescent periods, and the polarity of the constant current is alternated in successive stimulus events.

The described arrangements have some disadvantages. The system 20 includes complex circuitry in two locations, and care is required in order to balance charge. Data to configure Unit 2 is transferred during times of non-stimulus (e.g. between stimulus). Care is needed in regulation of logic voltages inside Unit 2, which is powered solely from the signal received from unit 1.

Some advantages of the system 20 include the fact that no net DC passes through the power cable 24. Data and power are passed together. Unit 1 can monitor the voltage on Unit 2. Under normal circumstances (i.e. no faults) an increased load within Unit 2 is readily seen by Unit 1 in the form of increased voltage on the supply line 24, affording the possibility of reverse telemetry.

The invention is not limited to any particular implementation of therapeutic medical implant, but for purposes of illustration, the example of a cochlear implant is described with reference to the functional block diagram illustrated in FIG. 4.

External Sensor and Processor 100 includes a microphone for the acquisition of sound, and electronics that process the sound, by one of a potential variety of means, into stimulation events to be delivered by a nerve stimulator including units 4-11 implanted within the user's body. Functional modules 4, 5 and 6 correspond to Unit 1 in FIG. 1, and functional modules 9 and 10 correspond to Unit 2. Wires 7 and 8 provide an interface between Unit 1 and Unit 2, or in this example between the governing circuit 5 and the rectifier/power storage/data extraction module 9 of unit 2.

The stimulation events are typically defined by the shape of the stimulus waveform to be delivered to the biological tissue. For purposes of this example, these waveforms are described by their current amplitude and phase duration of which two phases are delivered in each stimulation event. The two phases typically contain equal but opposite charge to one another so as to provide charge-balance at the end of each stimulation event. In neuroprosthesis maintaining a charge balance is beneficial for longevity of both the electrodes 11 and the biological tissue that the electrodes stimulate.

Once defined, the stimulus waveform definitions are encoded for transmission by any appropriate means including, but not limited to, a sequence of logical bits that is broadcast from the External Encoder Transmitter 2. The encoded data is delivered via Data and Power Link 3 which is typically a pair of inductively-coupled coils, one within and one outside of the body, separated for example by skin. Alternatively this could be by wire directly penetrating through the skin and connected to the implanted components. In some arrangements the implant system may include more than one RF link to implanted devices. For example, the patient may have one RF link located behind his or her ear, and another RF link located near the eye to transmit power and data to a vision implant that is implanted within the eye.

The encoded data sent via signals on Data and Power Link 3 from External Encoder Transmitter 2 to Rectifier Power Storage Data Extraction 4 contain the instructions that define the electrical stimulation to be delivered to the biological tissue from the electrodes 11. Moreover, these data also contain energy that can be extracted by way of rectification of the alternating signals received by Rectifier Power Storage Data Extraction 4 wherein a storage device such as a capacitor or battery is charged from the rectified data signals received. Decoding and data signals sent via 3 again define the stimulus to be delivered from the electrodes 11. The Governing Circuit 5 as part of its functionality, manages these data. As the stimulation parameters are known within 5, the behaviour of the remainder of the circuit—specifically that of the Rectifier Power Storage Data Extraction 9 and Multiplexing and Stimulus Generation Circuit 10 can be anticipated, and the appropriate energy applied to it when needed (Attribute 1).

As described above, Governing Circuit 5 determines the behaviour of 9 and 10 such that these modules of Unit 2 will, in turn, deliver the electrical stimulation to the user via electrodes 11. Governing circuit 5 instructs modules 9 and 10 by way of a two-wire interface, the wires of which are designated 7 and 8. Whenever possible, the signals carried on 7 and 8 are constant current (while at any one polarity), and of opposite polarity to one another at any instant in time. Moreover, the signals carried on 7 and 8 change their polarity simultaneously. By changing polarity for equal periods at each polarity, the net direct current (DC) on each wire (7 or 8) is nullified (Attributes 2 and 3).

Upon arrival at Rectifier Power Storage Data Extraction module 9 the signals carried on wires 7 and 8 are rectified to provide electrical energy to drive the circuit comprising both 9 and 10. Module 10 serves to create the electrical signals to be emitted by the electrodes 11. The magnitude of the electrical energy rectified from 7 and 8 is limited in current by governing circuit 5 according to the requirement of the electrical stimulation to be delivered from 11, and the requirements of the circuitry of Unit 2. Again, the required magnitude of electrical energy is known at 5 and may therefore be limited accordingly.

With an important objective being to minimize the physical size of modules 9 and 10 it is advantageous to avoid the need for 9 and 10 to consist of anything more than a microchip because discrete capacitors, resistors, etc. are relatively large. A typical rectification circuit, such as that contained in one arrangement within 4 comprises some storage method such as a large capacitor or battery that would be undesirable to be contained within 9. By delivering the appropriate amount of energy on wires 7 and 8 and switching the polarity of the signals on these wires only at times of minimized loading (e.g. when no electrical stimulation is taking place), the role played by the large capacitor becomes unnecessary, and relatively small, on-chip capacitors suffice for the needs of the rectification circuitry in Unit 2 (Attributes 2 and 3).

Multiplexing within 10 is achieved by opening and closing switches within the circuit according to instructions received via 7 and 8. Ultimately, electrical stimulation is delivered from the electrodes 11 as illustrated by the dashed arrows between electrodes. Should a fault mode exist (e.g. insulation failure at any point in the circuit comprising 7-11) the result of limiting the current passed to this part of the circuit in 5 is that current flow is no more than would have otherwise flowed through the tissue had there been no fault (Attribute 4).

Cable Interface Monitor 6 in Unit 1 measures the voltage and current passed via 7 and 8. This measurement allows Unit 1 to detect actions performed by Unit 2 (for example when Unit 2 has ceased stimulation). This, in combination with knowledge of the anticipated behaviour of Unit 2 (known within 5), allows for sensing of deviations of said anticipated behaviour and allows for remedial action to be taken (Attribute 5).

Within 10 in unit 2, a high-impedance operational amplifier (or other appropriate circuitry) is connected to one or more (e.g. all) electrodes after each event of electrical stimulation. After shortening all electrodes to the same electrical potential, no current should flow under normal conditions. Should current be detected, it would be indicative of a fault and would allow for (e.g.) a high load to be placed across 7 and 8 to alert the Governing Circuit 5 of the fault and to initiate remedial action being taken (Attribute 6).

Current passing from 5 to 9 along 7 and 8 may do so via decoupling capacitors within 5 (or 9, but less desirable there owing to size constraints). In this case, any charge imbalance will manifest itself in a rapid change in voltage across the current source or sink that is out of balance with the other. This will, in turn, cause said current source or sink to enter into voltage compliance and thus guarantee charge balance (Attribute 7).

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A system for transferring data and power between electronic devices implanted in a patient, the system comprising:
   a first unit and a second unit that in use are both implanted in the patient; and
   a cable connecting the first unit and the second unit,
   wherein the first unit comprises:
   a current supply unit that supplies a selected current output transferring data and power to the second unit via the cable, wherein the current output is a square current waveform having intermittent transitions of polarity that encode the data as a series of pulses; and
   a processor configured to anticipate an action to be performed by the second unit and to select the current output dependent on the anticipated action
   and wherein the second unit does not comprise a discrete capacitor.

2. A system according to claim 1 wherein the processor selects the current output from the group consisting of:
   a quiescent current output that has a magnitude sufficient to power the second unit in a quiescent state; and
   a stimulation current output that has a magnitude matched to an expected power requirement for the second unit to perform the anticipated action.

3. A system according to claim 2 wherein the data is encoded in the quiescent current output supplied to the second unit.

4. A system according to claim 1 wherein the second unit comprises a rectifier to rectify the current output received via the cable to power the second unit.

5. A system according to claim 1 wherein the processor changes the polarity to thereby encode the data while the loading of the current supply unit is below a minimum threshold.

6. A system according to claim 5 wherein the second unit consists of a protective housing and a single integrated circuit.

7. A system according to claim 1 comprising:
   one or more electrodes operable to apply stimulus signals to biological tissue of the patient, the second unit comprising a stimulus controller to control operation of the one or more electrodes.

8. A system according to claim 7 wherein the stimulus controller controls the one or more electrodes dependent on control information in the data received from the first unit via the cable.

9. A system according to claim 8 wherein the stimulus controller comprises a current limiter such that a current to the one or more electrodes is negligible unless the received control information specifies stimulation by the one or more electrodes.

10. A system according to claim 9 wherein the current limiter comprises a push-pull circuit.

11. A system according to claim 8 comprising a current measuring unit that monitors a current in at least one electrode after stimulation of the at least one electrode has ended, wherein the second unit alerts the first unit to a fault condition if the monitored current exceeds a threshold.

12. A system according to claim 1 wherein the cable comprises two wires and the first unit comprises a voltage measuring unit that measures a voltage across the wires.

13. A system according to claim 12 wherein the processor compares the measured voltage across the wires to an anticipated voltage associated with the anticipated action of the second unit.

14. A system according to claim 13 wherein the processor takes remedial action if the measured voltage differs from the anticipated voltage, the remedial action including at least one of:
   reducing the output current of the current supply unit;
   stopping the output current of the current supply unit; and
   limiting the voltage across the wires.

15. A system according to claim 1 comprising means for reducing a charge imbalance between the first unit and the second unit.

16. A system according to claim 15 wherein the means for reducing charge imbalance comprises at least one capacitor connected in series between the current supply unit and the cable.

17. A system according to claim 15 wherein the current output supplied by the first unit to the second unit is intermittently reversed in polarity and the system acts to equalise an accumulated time spent at each polarity.

18. A system according to claim 1 wherein the cable comprises two wires joining the first unit and the second unit, wherein in use the current supply unit supplies each wire with a current equal in magnitude and opposite in polarity to the current carried by the other wire.

19. A system according to claim 18 wherein the first unit comprises switching to reverse the polarity of the current carried by the wires, the switching acting to reverse the polarity of the wires substantially simultaneously.

20. A system according to claim 18 wherein the processor selects the magnitude of the current supplied to the two wires dependent on an anticipated power requirement of the second unit.

21. A system according to claim 1 wherein the second unit consists of a protective housing and a single integrated circuit.

22. A system for transferring data and power between electronic devices implanted in a patient, the system comprising:
   a first unit and a second unit that in use are both implanted in the patient,
   wherein the second unit does not comprise a discrete capacitor; and
   a cable connecting the first unit and the second unit,
   wherein the first unit comprises:
   a current supply unit that supplies a selected current output to provide data and power to the second unit via the cable, wherein the current output is a square current waveform in which the data is encoded as a series of pulses; and
   a processor configured to intermittently reverse a polarity of the supplied current, wherein the processor reverses the polarity to thereby encode the data only while a loading of the current supply unit is at or near a minimum.

23. A method for transferring data and power via a cable comprising two wires between a first implanted unit and a second implanted unit implanted in a patient, the method comprising:
   anticipating an action to be taken by the second implanted unit; and
   selecting a current output to be output by the first implanted unit to transfer data and power via the cable to the second implanted unit, wherein the selection is dependent on an expected power requirement of the second implanted unit for the anticipated action and wherein the current output is a square current waveform having intermittent transitions of polarity that encode the data as a series of pulses.

\* \* \* \* \*